United States Patent [19]
Nielsen

[11] Patent Number: 6,036,983
[45] Date of Patent: Mar. 14, 2000

[54] METHOD OF OBTAINING PROTEIN HYDROLYSATES

[75] Inventor: Per Munk Nielsen, Hillerød, Denmark

[73] Assignee: Novo Nordisk A/S, Bagsvaerd, Denmark

[21] Appl. No.: 09/188,985

[22] Filed: Nov. 9, 1998

Related U.S. Application Data

[63] Continuation of application No. PCT/DK97/00230, May 20, 1997.

[30] Foreign Application Priority Data

May 20, 1996 [DK] Denmark ............................. 0585/96

[51] Int. Cl.$^7$ ................................ C12P 21/06; A23J 3/34
[52] U.S. Cl. ................................ 426/53; 426/20; 426/42; 426/54; 426/56; 426/63; 426/656; 435/68.1; 435/212; 435/219
[58] Field of Search ................................ 426/42, 20, 53, 426/54, 56, 63, 656, 657; 435/212, 213, 219, 221, 220, 223, 227, 228, 68.1

[56] References Cited

U.S. PATENT DOCUMENTS

| | | | |
|---|---|---|---|
| 3,857,967 | 12/1974 | Kikuchi et al. | ............................. 426/18 |
| 5,082,672 | 1/1992 | Hamada et al. | ............................. 426/7 |

FOREIGN PATENT DOCUMENTS

| | | |
|---|---|---|
| 0 480 104 A1 | 4/1992 | European Pat. Off. . |
| WO 91/13554 | 9/1991 | WIPO . |

OTHER PUBLICATIONS

Mimouni et al. (1994) Journal of Cereal Science 21:153–165.
Drapeau et al. (1972) The Journal of Biological Chemistry 247(20):6720–6726.
Mosolova et al. (1987) Biokhimiya 52(3):414–422.
Yoshida et al. (1988) J. Biochem. 104:451–456.
Khaidarova et al. (1989) Biorak 54(1):1–60.
Niidome et al. (1990) J. Biochem. 108:965–970.
Chobert et al. (1988) J. Agric. Food Chem. 36:220–224.
Kikuchi et al. (1973) Agr. Biol. Chem. 37(4):719–724.

*Primary Examiner*—Keith D. Hendricks
*Attorney, Agent, or Firm*—Steve T. Zelson; Valeta Gregg

[57] ABSTRACT

The present invention relates to a method of obtaining protein hydrolysates useful as flavoring agents. More specifically, the invention provides a method of obtaining from a proteinaceous sustrate a hydrolysate enriched in free glutamic acid and/or peptide bound glutamic acid residues, which method comprises the steps of subjecting the substrate to a deamidation process, and subjecting the substrate to the action of a specific acting proteolytic enzyme.

39 Claims, No Drawings

METHOD OF OBTAINING PROTEIN HYDROLYSATES

CROSS-REFERENCE TO RELATED APPLICATIONS

This application is a continuation of PCT/DK97/00230 filed May 20, 1997 which claims priority under 35 U.S.C. 119 of Danish application 0585/96 filed May 20, 1996, the contents of which are fully incorporated herein by reference.

TECHNICAL FIELD

The present invention relates to a method of obtaining protein hydrolysates useful as flavoring agents. More specifically, the invention provides a method of obtaining from a proteinaceous substrate a hydrolysate enriched in free glutamic acid and/or peptide bound glutamic acid residues, which method comprises the steps of subjecting the substrate to a deamidation process, and subjecting the substrate to the action of a specific acting proteolytic enzyme.

BACKGROUND ART

Various food products, e.g. soups, sauces and seasonings, comprises flavoring agents obtained by hydrolysis of proteinaceous materials. Conventionally this hydrolysis is brought about using strong hydrochloric acid, followed by neutralization with sodium hydroxide. However, such chemical hydrolysis leads to severe degradation of the amino acids obtained during the hydrolysis, and also to hazardous byproducts formed in the course of this chemical reaction. Therefore increasing concern over the use of flavoring agents obtained by chemical hydrolysis has lead to the development of enzymatic hydrolysis processes.

Enzymatic hydrolysis processes aim at obtaining a high degree of hydrolysis (DH), and this is usually attained using a complex of unspecific acting proteolytic enzymes (i.e. unspecific acting endo- and exo-peptidases). In this way e.g. WO 94/25580 describes a method for hydrolyzing proteins by use of an unspecific acting enzyme preparation obtained from *Aspergillus oryzae*. Specific acting proteolytic enzymes have not been used for this purpose, because such enzymes only lead to an inadequate degree of hydrolysis.

Only relatively few specific acting proteolytic enzymes have been reported. Thus proteolytic enzymes preferentially cleaving peptides at glutamoyl-peptide bonds (Glu-specific proteases) obtained from *Staphylococcus aureus* [Drapeau G R, Boily Y and Houmard J; *J. Biol. Chem.* 1972 247 (20) 6720–6726], from Actinomyces sp. [Mosolova O V, Rudenskaya G N, Stepanov V M, Khodova O M and Tsaplina I A; *Biokhimiya* 1987 52 (3) 414–422], from *Streptomyces griseus* [Yoshida N, Tsuruyama S, Nagata K, Hirayama K, Noda K and Makisumi S; *J. Biochem.* 1988 104 451–456], from *Streptomyces thermovulgaris* [Khaldarova N Y, Rudenskaya G N, Revina L P, Stephanov V M and Egorov N S; *Biochimiia Moscow Eng.* 1989 54 (1) 32–38], from *Bacillus subtilis* [Niidome T, Yoshida N, Ogata F, Ito A and Noda K; *J. Biochem.* 1990 108 965–970], and from *Bacillus licheniformis* [WO 91/13554 A1], have been reported.

Glu-specific proteases primarily find applications in studies of protein structures. However, use of a Glu-specific *Staphylococcus aureus* protease for modifying the solubility and structural properties of casein has been reported [Chobert J-M, Sitohy M Z and Whitaker J R; *J. Agric. Food Chem.* 1988 36 220–224], and WO 91/13554 A1 describes the use of the *Bacillus licheniformis* for obtaining a limited specific hydrolysis of proteins.

Whereas glutamine (Gln) is almost tasteless, glutamic acid (Glu), whether free or peptide bound, plays an important role for the flavor and palatability of protein hydrolysates. Glutamic acid may be formed by converting free glutamine to glutamic acid. This conversion (i.e. deamidation) is inherently taking place during conventional chemical hydrolysis using strong hydrochloric acid.

Alternatively glutamic acid may be formed from free glutamine by the action of a glutaminase (L-Glutaminase, EC 3.5.1.22 or D-Glutaminase, EC 3.5.1.35). However, substantial amounts of the glutamine may be lost as it spontaneously converts to pyroglutamine.

In contrast to glutaminase, peptidoglutaminase (PGases) acts on peptide bound glutamine. Two types of peptidoglutaminases are known. Peptidyl-glutaminase (EC 3.5.1.43; Peptidoglutaminase I) specific for glutamine substituted at the α-amino group, and Protein-glutamine glutaminase (EC 3.5.1.44; Peptidoglutaminase II) specific for glutamine substituted at the carboxyl position or both the α-amino and carboxyl positions. Peptidoglutaminases obtained from *Aspergillus japonicus*, *Bacillus circulans*, *Cryptococcus albidus*, and *Debaryomyces kloecheri* have been reported [Kikuchi M & Sakaguchi K; *Agr. Biol. Chem.* 1973 37 (4) 719–724].

Peptidoglutaminases are known and useful for modifying food proteins. Structural modifications of proteins improve their functional properties and extends their use as food ingredients. Thus U.S. Pat. No. 5,082,672 describes a method of treating food proteins by deamidation with a peptidoglutaminase, by which method the solubility, emulsification, foaming and other functional properties of soy proteins become improved. However, U.S. Pat. No. 5,082,672 also report that the ability of peptidoglutaminase to deamidate intact soy protein is limited due to its large molecular size and/or unique conformation. Therefore U.S. Pat. No. 5,082,672 teach initial degradation of the substrate by hydrolysis with Alcalase™, an un-specific acting endo/exo-peptidase complex obtained from *Bacillus licheniformis*, and/or heat treatment, and find that pre- and post-heat treatment of hydrolyzed soy protein produced the greatest degree of deamidation.

U.S. Pat. No. 3,857,967 describes a process for preparing food and beverages with a peptidoglutaminase obtained from *Bacillus circulans*. Also, in order to obtain the greatest degree of deamidation, U.S. Pat. No. 3,857,967 teach initial degradation of the proteinaceous substrate by use of un-specific acting endo/exo-peptidases.

Mimouni et al. [Mimouni B, Raymond J, Merle-Desnoyers A M, Azanza J L & Ducastaing A; *Journal of Cereal Science* 1994 21 153–165] describe a combined acid deamidation and enzymatic hydrolysis for improvement of the functional properties of wheat gluten. More particularly, Mimouni et al. describe acid deamidation combined with the use of unspecific acting endo-peptidases.

SUMMARY OF THE INVENTION

It has now been found that protein hydrolysates of excellent flavor and functionality can be obtained by subjecting the proteinaceous material to the combined action of a deamidation process and the action of a specific acting proteolytic enzyme.

Accordingly the present invention provides a method of obtaining from a proteinaceous substrate a hydrolysate enriched in free glutamic acid and/or peptide bound glutamic acid residues, which method comprises the steps of subjecting the substrate to a deamidation process; and subjecting the substrate to the action of a specific acting proteolytic enzyme.

In a preferred embodiment, the invention provides a method for obtaining from a proteinaceous substrate a hydrolysate enriched in glutamic acid, which method comprises the steps of subjecting the substrate to the action a peptidoglutaminase and subjecting the substrate to the action of a proteolytic enzyme preferentially cleaving glutamoyl-peptide bonds, followed by the action of one or more unspecifically acting endo- and/or exo-peptidase enzymes.

DETAILED DISCLOSURE OF THE INVENTION

The present invention relates to a method of obtaining a hydrolysate enriched in free glutamic acid and/or peptide bound glutamic acid residues, which method comprises the steps of
 (i) subjecting the substrate to a deamidation process; and
 (ii) subjecting the substrate to the action of a specific acting proteolytic enzyme.

The two steps, (i) and (ii), may be accomplished simultaneously, or step (ii) may be performed subsequent to step (i).

By the method of the invention protein hydrolysates of excellent flavor and functionality can be obtained. In particular protein hydrolysates of excellent flavor can be obtained because glutamic acid (Glu), whether free or peptide bound, plays an important role for the flavor and palatability of protein hydrolysates. However, by the method of the invention protein hydrolysates of improved functionality can also be obtained, in particular with respect to improved solubility, improved emulsifying properties, increased degree of hydrolysis and improved foaming properties.

Deamidation Processes

The conversion of amides (glutamine or asparagine) into charged acids (glutamic acid or aspartic acid) via the liberation of ammonia is known as deamidation. Deamidation may take place as a non-enzymatic or as an enzymatic deamidation process.

In a preferred embodiment the deamidation is carried out as an enzymatic deamidation process. In particular the enzymatic may be carried out by subjecting the substrate to the action of a transglutaminase or the action of a peptidoglutaminase.

Transglutaminases

In a preferred embodiment the deamidation is carried out as an enzymatic deamidation process in which the substrate is subjected to the action of a transglutaminase. The transglutaminase may be of any convenient source including those derived from mammals, see e.g. JP 1050382 and JP5023182, including activated Factor XIII, see e.g. WO 93/15234; those derived from fish, see e.g. EP 555,649; and those derived from microorganisms, see e.g. EP 379,606, WO 96/06931 and WO 96/22366.

In another specific embodiment, the transglutaminase is derived from an Oomycete, including a strain of Phytophthora, in particular *Phytophthora cactorum*, a strain of Pythium, in particular *Pythium irregulare*, Pythium sp., *Pythium intermedium, Pythium ultimum*, and *Pythium periilum* (or *P. periplocum*).

In yet another specific embodiment, the transglutaminase is of bacterial origin and is preferably derived from a strain of Bacillus, in particular *Bacillus subtilis*, a strain of Streptoverticillium, in particular *Streptoverticillium mobaraensis, Streptoverticillium griseocameum, Streptoverticillium cinnamoneum*, and a strain of Streptomyces, in particular *Streptomyces lydicus*.

The transglutaminase shall be added to the proteinaceous substrate in effective amounts. The transglutaminase may be added in amounts conventionally employed in deamidation processes. It is at present contemplated that an effective amount of transglutaminase is in the range of from about 0.01 to about 5% (w/w) of enzyme preparation relating to the amount of substrate, preferably in the range of from about 0.1 to about 1% (w/w) of enzyme preparation relating to the amount of substrate.

The enzymatic treatment (incubation) may take place at any convenient temperature at which the enzyme preparation does not become inactivated, preferably in the range of from about 20° C. to about 70° C.

In accordance with established practice the enzyme preparation may suitably be inactivated by increasing the temperature of the incubation mixture to a temperature where the enzymes become inactivated, e.g. to above about 70° C., or similarly by decreasing the pH of the incubation mixture to a value where the enzymes become inactivated, e.g. below about 4.0.

Peptidoglutaminases

In another preferred embodiment the deamidation is carried out as an enzymatic deamidation process in which the substrate is subjected to the action of a peptidoglutaminase.

In a more specific embodiment, the peptidoglutaminase used in the method of the invention may be a peptidoglutaminase I (peptidyl-glutaminase; EC 3.5.1.43), or a peptidoglutaminase II (protein-glutamine glutaminase; EC 3.5.1.44), or any mixture hereof. The peptidoglutaminase may be derived from a strain of Aspergillus, in particular a strain of *Aspergillus japonicus*, a strain of Bacillus, in particular a strain of *Bacillus circulans*, a strain of Cryptococcus, in particular a strain of *Cryptococcus albidus*, or a strain of Debaryomyces, in particular a strain of *Debaryomyces kloecheri*.

The peptidoglutaminase shall be added to the proteinaceous substrate in effective amounts. The peptidoglutaminase may be added in amounts conventionally employed in deamidation processes. It is at present contemplated that an effective amount of peptidoglutaminase is in the range of from about 0.01 to about 100.000 PGase Units per 100 g of substrate, in particular in the range of from about 0.1 to about 10.000 PGase Units per 100 g of substrate.

The enzymatic treatment (incubation) may take place at any convenient temperature at which the enzyme preparation does not become inactivated, preferably in the range of from about 20° C. to about 70° C.

In accordance with established practice the enzyme preparation may suitably be inactivated by increasing the temperature of the incubation mixture to a temperature where the enzymes become inactivated, e.g. to above about 70° C., or similarly by decreasing the pH of the incubation mixture to a value where the enzymes become inactivated, e.g. below about 4.0.

Specific Acting Proteolytic Enzymes

The method of the invention comprises the step of subjecting the substrate to the action of a specific acting proteolytic enzyme. More specifically the specific acting proteolytic enzyme may be a specific acting endo-peptidase or a specific acting exo-peptidase. The specific acting proteolytic enzyme may be of any available source.

Endo-peptidases

In a preferred embodiment the specific acting proteolytic enzyme is an endopeptidase such as
 (i) a glutamyl endopeptidase (EC 3.4.21.19);
 (ii) a lysyl endopeptidase (EC 3.4.21.50);
 (iii) a leucyl endopeptidase (EC 3.4.21.57);

(iv) a glycyl endopeptidase (EC 3.4.22.25);

(v) a prolyl endopeptidase (EC 3.4.21.26);

(vi) trypsin (EC 3.4.21.4) or a trypsin-like (lysine/arginine specific) endopeptidase; or (vii) a peptidyl-Asp metalloendopeptidase (EC 3.4.24.33).

The glutamyl endopeptidase (EC 3.4.21.19) of item (i) i.e. a proteolytic enzyme preferentially cleaving glutamoyl-peptide bonds, may preferably be derived from a strain of Bacillus, in particular *Bacillus licheniformis* and *Bacillus subtilis*, a strain of Staphylococcus, in particular *Staphylococcus aureus*, a strain of Streptomyces, in particular *Streptomyces thermovulgaris* and *Streptomyces griseus*, or a strain of Actinomyces sp.

The lysyl endopeptidase (EC 3.4.21.50) of item (ii) may preferably be derived from a strain of Achromobacter, in particular *Achromobacter lyticus*, a strain of Lysobacter, in particular *Lysobacter enzymogenes*, or a strain of Pseudomonas, in particular *Pseudomonas aeruginosa*.

The leucyl endopeptidase (EC 3.4.21.57) of item (iii) may be of plant origin.

The glycyl endopeptidase (EC 3.4.22.25) of item (iv) may preferably be derived from the papaya plant (*Carica papaya*).

The prolyl endopeptidase (EC 3.4.21.26) of item (v) may preferably be derived from a strain of Flavobacterium, or it may be of plant origin.

The trypsin-like endopeptidase of item (vi) may preferably be derived from a strain of Fusarium, in particular *Fusarium oxysporum*, e.g. as described in WO 89/06270 or WO 94/25583.

The peptidyl-Asp metalloendopeptidase (EC 3.4.24.33) of item (vii) may preferably be derived from a strain of Pseudomonas, in particular *Pseudomonas fragi*.

Exo-peptidases

In another preferred embodiment the specific acting proteolytic enzyme is an exo-peptidase enzyme that may act from either ends of the peptide, i.e. may be a aminopeptidase or it may be a carboxypeptidase.

In a preferred embodiment, the specific acting proteolytic enzyme is an aminopeptidase such as (i) a leucyl aminopeptidase (EC 3.4.11.1); or (ii) a tripeptide aminopeptidase (EC 3.4.11.4).

In another preferred embodiment, the specific acting proteolytic enzyme is a carboxypeptidase such as (i) a proline carboxypeptidase (EC 3.4.16.2);

(ii) a carboxypeptidase A (EC 3.4.17.1);

(iii) a carboxypeptidase B (EC 3.4.17.2);

(iv) a carboxypeptidase C (EC 3.4.16.5);

(v) a carboxypeptidase D (EC 3.4.16.6);

(vi) a lysine(arginine) carboxypeptidase (EC 3.4.17.3);

(vii) a glycine carboxypeptidase (EC 3.4.17.4);

(viii) an alanine carboxypeptidase (EC 3.4.17.6);

(ix) a glutamate carboxypeptidase (EC 3.4.17.11);

(x) a peptidyl-dipeptidase A (EC 3.4.1 5.1); or (xi) a peptidyl-dipeptidase (EC 3.4.15.5).

The specific acting endo- or exo-peptidase enzyme shall be added to the proteinaceous substrate in a effective amount. The proteolytic may be added in amounts conventionally employed in protein hydrolysis processes. It is at present contemplated that an effective amount of endo-peptidase is in the range of from about 0.05 to about 15 CPU/100 g of substrate, in particular in the range of from about 0.1 to about 5 CPU/100 g of substrate, and an effective amount of exo-peptidase is in the range of from about 0.001 to about 0.5 AU/100 g of substrate, in particular in the range of from about 0.01 to about 0.1 AU/100 g of substrate.

The enzymatic treatment (incubation) may take place at any convenient temperature at which the enzyme preparation does not become inactivated, preferably in the range of from about 20° C. to about 70° C.

In accordance with established practice the enzyme preparation may suitably be inactivated by increasing the temperature of the incubation mixture to a temperature where the enzymes become inactivated, e.g. to above about 70° C., or similarly by decreasing the pH of the incubation mixture to a value where the enzymes become inactivated, e.g. below about 4.0.

Unspecific Acting Proteolytic Enzymes

In a more specific embodiment, the method of the invention comprises the additional step of (iii) subjecting the substrate to the action of one or more unspecific acting endo- and/or exo-peptidase enzymes.

In this step the substrate is subjected to a conventional hydrolysis step. This additional step may take place simultaneously with steps (i) and (ii), or it may be accomplished subsequent to steps (i) and (ii). In particular the substrate may be the reaction mixture of steps (i) and (ii).

In a preferred embodiment the unspecific acting endo- and/or exo-peptidase enzyme is derived from a strain of Aspergillus, in particular a strain of *Aspergillus niger*, a strain of *Aspergillus oryzae*, or a strain of *Aspergillus soyae*, or a strain of Bacillus, in particular a strain of *Bacillus amyloliquefaciens*, a strain of *Bacillus lentus*, a strain of *Bacillus licheniformis* or a strain of *Bacillus subtilis*.

The unspecific acting endo- and/or exo-peptidase enzyme is added to the substrate in amounts in the range of from about 0.05 to about 15 CPU/100 g of substrate, in particular in the range of from about 0.1 to about 5 CPU/1 00 g of substrate.

The enzymatic treatment (incubation) may take place at any convenient temperature at which the enzyme preparation does not become inactivated, preferably in the range of from about 20° C. to about 70° C.

In accordance with established practice the enzyme preparation may suitably be inactivated by increasing the temperature of the incubation mixture to a temperature where the enzymes become inactivated, e.g. to above about 70° C., or similarly by decreasing the pH of the incubation mixture to a value where the enzymes become inactivated, e.g. below about 4.0.

Proteinaceous Substrates

The proteinaceous substrate subjected to the method of the present invention may consist of intact proteins, or it may consist of pre-hydrolyzed proteins (peptides), or it may be a mixture hereof. Also, the proteinaceous substrate may be vegetable or of animal origin.

Preferably the proteinaceous substrate is of vegetable origin, and may in particular be soy protein, grain protein, e.g. wheat gluten, corn gluten, barley, rye, oat, rice, zein, cotton seed protein, rape seed protein, peanut, alfalfa protein, pea protein, fabaceous bean protein, sesame seed protein, or sunflower.

A proteinaceous substrate of animal origin may in particular be whey protein, casein, meat proteins, fish protein, red blood cells, egg white, gelatin, or lactoalbumin.

Industrial Applications

The hydrolysates enriched in free glutamic acid and/or peptide bound glutamic acid residues obtained by the method of the invention may be used in various industrial applications, in particular where there is a need for the incorporation of functional proteins.

Therefore, in another aspect, the present invention provides a food product comprising a hydrolysate enriched in free glutamic acid and/or peptide bound glutamic acid residues obtained by the method of the invention.

In yet another aspect, the invention provides an animal feed additive comprising a hydrolysate enriched in free glutamic acid and/or peptide bound glutamic acid residues obtained by the method of the invention.

Assay for Enzymatic Activity
Peptidoglutaminase Activity

The peptidoglutaminase activity may determined according to the procedure of Cedrangoro et al. [Cedrangoro et al.; *Enzymologia* 1965 29 143], and as described in U.S. Pat. No. 3,857,967.

According to this method, 0.5 ml of an enzyme sample, adjusted to pH 6.5 with 1N NaOH, is charged into a small vessel. Following the procedure of Cedrangoro et al., 1 ml of a borate buffer solution, pH 10.8, is added to the vessel, the discharged ammonia is absorbed by 5N sulphuric acid, and the mixture is allowed to form colour by use of Nessler's reagent, and the light absorptivity of the formed colour is measured at 420 mγ.

One PGase unit is the amount of enzyme capable of producing 1 γmol/minute of ammonia under these conditions.

Alternatively, the peptidoglutaminase activity may determined according to the procedure described in Example 2, below.

Proteolytic Activity: Casein Protease Units (CPU)

The proteolytic activity may be determined using casein as substrate. One Casein Protease Unit (CPU) is defined as the amount of enzyme liberating 1 mM of primary amino groups (determined by comparison with a serine standard) per minute under standard conditions, i.e. incubation for 30 minutes at 25° C. and pH 9.5.

A folder AF 228/1 describing this analytical method in more detail is available upon request to Novo Nordisk A/S, Denmark, which folder is hereby included by reference.

Proteolytic Activity: Anson Units (AU)

The proteolytic activity may alternatively be determined with denatured haemoglobin as substrate. In the Anson-Haemoglobin method for the determination of proteolytic activity denatured haemoglobin is digested, and the undigested haemoglobin is precipitated with trichloroacetic acid (TCA). The amount of TCA soluble product is determined with phenol reagent, which gives a blue colour with tyrosine and tryptophan.

One Anson Unit (AU) is defined as the amount of enzyme which under standard conditions (i.e. 25° C., pH 7.5 and 10 min. reaction time) digests haemoglobin at an initial rate such that there is liberated per minute an amount of TCA soluble product which gives the same colour with phenol reagent as one milli-equivalent of tyrosine.

A folder AF 4/5 describing the analytical method in more detail is available upon request to Novo Nordisk A/S, Denmark, which folder is hereby included by reference.

Proteolytic Activity: Leucine Amino Peptidase Units (LAPU)

The proteolytic activity may alternatively be determined with leucine-p-nitroanilide as substrate. Upon hydrolysis p-nitroanilide is liberated turning the solution yellow. The activity is determined using p-nitroanilide as chromophore, the yellow colour produced being photometered at 405 nm.

1 Leucine Amino Peptidase Unit (LAPU) is the amount of enzyme which decomposes 1μ(micro)M substrate per minute at the following conditions: 26 mM of L-leucine-p-nitroanilide as substrate, 0.1 M Tris buffer (pH 8.0), 40° C., 10 minutes reaction time.

EXAMPLES

The invention is further illustrated in the following examples which are not intended to be in any way limiting to the scope of the invention as claimed.

Example 1

Increased Protein Solubility and Release of Glutamate by Deamidation
Hydrolysis

Wheat gluten (WG) was obtained from Cargill (JOB 5141) and deamidated wheat gluten (DWG) was obtained from StaPro Consultancy B.V., Lemdijk 32, 9422 TH Smilde, NL. Suspensions of 8% protein were made by mixing 11 g of gluten with 89 g of water. The pH was adjusted to 6.5 with NaOH. Glutamate/aspartate specific protease (SP446), obtainable as described in WO 91/13554, or lysine/arginine specific protease (SP387) obtainable as described in WO 89/06270, was added to the suspensions. The dosage was 0.01 AU/g protein for SP446 and 0.006 AU/g protein for SP387. Flavourzyme™ (an un-specifically acting protease preparation available from Novo Nordisk A/S, Denmark, containing endo- and exo-peptidase activities, and obtained by fermentation of *Aspergillus oryzae*) was added to some of the hydrolysates at a dosage of 20 LAPU/g protein. The hydrolyses were carried out at 50° C. without further pH adjustment for 18 hours. The enzymes were inactivated by heating at 85° C. for 15 minutes. The pH was adjusted to 5 and the hydrolysates centrifuged. The content of protein and free glutamate in the supernatant was determined.

Determination of Protein

Protein was determined by Kjeldahl analysis, using a Kjeldahl factor of 6.25.

Determination of Glutamate

The content of free glutamate was determined by use of the Boehringer-Mannheim kit for glutamate determination (Cat. No. 139 092). The method was adapted for use in microtiter plates.

| | Results | | | |
|---|---|---|---|---|
| | Protein Solubility % | | Glutamate Content mg/l | |
| Hydrolysate | WG | DWG | WG | DWG |
| SP446 | 18 | 54 | 0 | 0 |
| SP387 | 35 | 44 | 0 | 0 |
| SP446 + Flavourzyme™ | 34 | 87 | 1000 | 2000 |

When comparing wheat gluten (WG) to deamidated wheat gluten (DWG), the results show that deamidation increase the susceptibility of the gluten to specific proteases, such that more protein becomes soluble. By addition of Flavourzyme™ on top of a specific protease the release of glutamate is doubled due to deamidation.

Example 2

Enzymatic Deamidation and Release of Glutamate
Fermentation of *Bacillus circulans*

*Bacillus circulans* cultures of the strain ATCC 21590 were grown in shake flasks of 400 ml capacity containing 200 ml of a medium composed of 1% polypeptone; 0.5% lactose; 0.025% $MgSO_4*7\ H_2O$; 0.005% $FeSO_4*7H_2O$; 0.025% $KH_2PO_4$; and 17% $Na_2HPO_4*12H_2O$, with the pH adjusted to 7.2. Fermentation took place at 30° C. for 20 hours using a stirring of 270 rpm. The cells were harvested by centrifugation at 4000 rpm in 1 liter flasks. The cells were frozen.
Purification of Peptidoglutaminase II from *Bacillus circulans*

All steps were performed at room temperature.

The frozen *Bacillus circulans* cells were thawed and suspended in Lysis buffer (50 mM Tris/HCl; 25% (w/v) sucrose; 1 mM EDTA, pH 8.0) until a homogeneous suspension was obtained—100 g wet cells per liter Lysis buffer. Lysozyme™ (Fluka 62971, 10 mg/ml) and DNAse I (Sigma DN-25, 10 mg/ml) were dissolved in Lysis buffer. 100 ml Lysozyme™ solution, 10 ml 1.0M MgCl2, and 1 ml DNAse I solution were added per liter cell suspension. The enzymes were allowed to act for 1 hour.

The suspension was filtered through a Seitz depth filter plate and the filtrate was transferred to a 10 mM KH2PO4/NaOH, pH 8.0 (Buffer A) on a Sephadex G25 column (Pharmacia). The enzyme solution was applied to a SOURCE Q column (Pharmacia) equilibrated in Buffer A and eluted with a linear NaCl gradient (0→500 mM) in Buffer A. Fractions from the column were analysed for Peptidoglutaminase II activity as described below and fractions with activity were pooled. The absorbance of the pooled fractions at 280 nm was 1.78, thus the protein content was estimated to 1.8 mg/ml.

The purity of the protein in the Peptidoglutaminase II pool was approx. 25% as judged from a SDS-PAGE gel. Thus the preparation contained approximately 0.5 mg/ml of pure peptidoglutaminase II.

Peptidoglutaminase Assay Method

The enzymatic activity is determined by measuring the ammonia formed during hydrolysis of y-carboxyamide of N-tert-Butoxycarbonyl (N-t-BOC-Gln-Pro; SIGMA No. B4403) using the Boehringer-Mannheim kit for ammonia determination (Cat. No. 1112732). In this kit, ammonia is measured by determination of the consumption of NADH by glutamate dehydrogenase, and blanks without the addition of N-t-BOC-Gln-Pro were also applied in order to subtract the effect of other NADH consuming enzymes.

Wheat Gluten Hydrolysis 200 mg of wheat gluten protein was added 9 ml of boiling water and after cooling, pH was adjusted to 7.0. Then 250 μl of the peptidoglutaminase II preparation (PEP) described above was added. The glutamate/aspartate specific protease (SP446) from example 1 was added in an amount of 0.04 AU/g protein, and Flavourzyme™ from example 1 was added at in an amount of 20 LAPU/g protein.

Hydrolysis proceeded without pH adjustment for 18 hours at 50° C. Blanks without addition of peptidoglutaminase were produced. The hydrolysates were centrifuged and glutamate was measured as described in Example 1.

The degree of hydrolysis (DH) of the wheat gluten protein was determined as described below Determination of the Degree of Hydrolysis (DH)

The DH of the protein, defined as described in by Adler-Nissen [Adler-Nissen J; *Enzymic Hydrolysis of Food proteins*; Elsevier Applied Science Publishers, 1986] was determined by reaction of the supernatant with OPA (orthophtaldialdehyde, Sigma). For the OPA reagent, 160mg of OPA was dissolved in 4 ml ethanol and transferred to a 200 ml volumetric flask containing a solution of 7.62 g di-sodium tetraborate decahydrate and 200 mg Sodium dodecylsulphate and 176 mg dithiothreitol and the flask was filled to the mark with water. The reagent is light sensitive.

25 μl of suitably diluted supernatant was mixed with 200 μl OPA reagent in a microtiter plate well and allowed to react for exactly 2 minutes at 25° C. The absorbance at 340 nm was measured in a microtiter plate reader and compared to the absorbance of a 95 mM L-serine standard solution after subtraction of the blank value (water reacted with OPA-reagent). To find the true DH, the serine equivalents measured in the supernatants were corrected with the factors suggested by Adler-Nissen for the Trinitrobenzenesulfonic acid method [Adler-Nissen J; *Agricultural and Food Chemistry*, 1979 27 (6) 1256] which give the same response as the described OPA method. The degree of hydrolysis was calculated on basis of the total amount of protein in the hydrolysis mixture (not on basis of soluble protein).

| | Results | |
|---|---|---|
| Hydrolysis | DH % | Glutamate mg/l |
| Minus PEP | 40 | 131 |
| Plus PEP | 43 | 171 |

As it is seen from the table, hydrolysis with the peptidoglutaminase preparation increase the DH as well as the release of glutamate.

What is claimed is:

1. A method of producing a deaminated hydrolysate from a proteinaceous substrate, comprising the steps of:
   (i) subjecting the substrate to a deamidation process;
   (ii) subjecting the substrate to the action of a specific acting proteolytic enzyme; and
   (iii) subjecting the substrate to the action of one or more unspecific acting endo- and/or exo-peptidase enzymes.

2. The method of claim 1, wherein the deamidation process is non-enzymatic.

3. The method of claim 1, wherein the deamidation process is enzymatic.

4. The method of claim 3, wherein the deamidation process is carried out with a transglutaminase.

5. The method of claim 4, wherein the transglutaminase is derived from a strain of Phytophthora or Pythium.

6. The method of claim 4, wherein the transglutaminase is bacterial.

7. The method of claim 6, wherein the transglutaminase is derived from a strain of Bacillus, Streptoverticillium, or Streptomyces.

8. The method of claim 3, wherein the deamidation process is carried with a peptidoglutaminase.

9. The method of claim 8, wherein the peptidoglutaminase is a peptidoglutaminase I (peptidyl-glutaminase; EC 3.5.1.43), or a peptidoglutaminase II (protein-glutamine glutaminase; EC 3.5.1.44), or a mixture thereof.

10. The method of claim 8, wherein the peptidoglutaminase is derived from a strain of Aspergillus, Bacillus, Cryptococcus or Debaryomyces.

11. The method of claim 8, wherein the peptidoglutaminase is added to the substrate in an amount from about 0.01 to about 100,000 PGase Units per 100 g of substrate.

12. The method of claim 11, wherein the peptidoglutaminase is added to the substrate in an amount from about 0.1 to about 10,000 PGase Units per 100 g of substrate.

13. The method of claim 1, wherein the specific acting proteolytic enzyme is an endo-peptidase.

14. The method of claim 13, wherein the endo-peptidase is selected from the group consisting of:
   (i) a glutamyl endopeptidase (EC 3.4.21.19);
   (ii) a lysyl endopeptidase (EC 3.4.21.50);

(iii) a leucyl endopeptidase (EC 3.4.21.57);

(iv) a glycyl endopeptidase (EC 3.4.22.25);

(v) a prolyl endopeptidase (EC 3.4.21.26);

(vi) trypsin (EC 3.4.21.4) or a trypsin-like endopeptidase; and (vii) a peptidyl-Asp metalloendopeptidase (EC 3.4.24.33).

15. The method of claim 14, wherein the glutamyl endopeptidase of (i) is derived from a strain of Bacillus, Staphylococcus, Streptomyces, or Actinomyces.

16. The method of claim 14, wherein the lysyl endopeptidase of (ii) is derived from a strain of Achromobacter, Lysobacter, of Pseudomonas.

17. The method of claim 14, wherein the glycyl endopeptidase of (iv) is derived from a papaya plant.

18. The method of claim 14, wherein the prolyl endopeptidase of (v) is derived from a strain of Flavobacterium.

19. The method of claim 14, wherein the trypsin-like endopeptidase of (vi) is derived from a strain of Fusarium.

20. The method of claim 19, wherein the strain is *Fusarium oxysporum*.

21. The method of claim 14, wherein the peptidyl-Asp metalloendopeptidase of (vii) is derived from a strain of Pseudomonas.

22. The method of claim 1, wherein the specific acting proteolytic enzyme is an exo-peptidase enzyme.

23. The method of claim 22, wherein the exo-peptidase is an aminopeptidase.

24. The method of claim 23, wherein the aminopeptidase is a leucyl aminopeptidase (EC 3.4.11.1) or a tripeptide aminopeptidase (EC 3.4.11.4).

25. The method of claim 22, wherein the exo-peptidase is a carboxypeptidase.

26. The method of claim 25, wherein the carboxypeptidase is selected from the group consisting of:

(i) a proline carboxypeptidase (EC 3.4.16.2);

(ii) a carboxypeptidase A (EC 3.4.17.1);

(iii) a carboxypeptidase B (EC 3.4.17.2);

(iv) a carboxypeptidase C (EC 3.4.16.5);

(v) a carboxypeptidase D (EC 3.4.16.6);

(vi) a lysine(arginine) carboxypeptidase (EC 3.4.17.3);

(vii) a glycine carboxypeptidase (EC 3.4.17.4);

(viii) an alanine carboxypeptidase (EC 3.4.17.6);

(ix) a glutamate carboxypeptidase (EC 3.4.17.11);

(x) a peptidyl-dipeptidase A (EC 3.4.15.1); and (xii) a peptidyl-dipeptidase (EC 3.4.15.5).

27. The method of claim 1, wherein the specific acting proteolytic enzyme is added to the substrate in an amount between about 0.05 and about 15 CPU/100 g of substrate.

28. The method of claim 1, wherein step (i) and step (ii) are performed simultaneously.

29. The method of claim 1, wherein step (i) is performed before step (ii).

30. The method of claim 1, wherein steps (i), (ii) and (iii) are performed simultaneously.

31. The method claim 1, wherein step (iii) is performed after steps (i) and (ii).

32. The method of claim 1, wherein the unspecific acting endo- and/or exo-peptidase enzyme of step (iii) is derived from a strain of Aspergillus or Bacillus.

33. The method of claim 1, wherein the unspecific acting endo- and/or exo-peptidase enzyme is added to the substrate in amounts in the range of from about 0.001 to about 15 CPU/100 g of substrate.

34. The method of claim 1, wherein the proteinaceous substrate is of a vegetable protein.

35. The method of claim 34, wherein the vegetable protein is selected from one of soy protein, wheat gluten, corn gluten, barley, rye, oat, rice, zein, cotton seed protein, rape seed protein, peanut, alfalfa protein, pea protein, fabaceous bean protein, sesame seed protein, and sunflower.

36. The method of claim 34, wherein the proteinaceous substrate is an animal protein.

37. The method of claim 36, wherein the animal protein is selected from one of whey protein, casein, meat proteins, fish protein, red blood cells, egg white, gelatin, and lactoalbumin.

38. A food product comprising a deamidated hydrolysate produced by the method of claim 34.

39. An animal feed additive comprising a deamidated hydrolysate produced by the method of claim 34.

* * * * *